US009289483B2

(12) United States Patent
Cardona Iglesias et al.

(10) Patent No.: US 9,289,483 B2
(45) **Date of Patent: *Mar. 22, 2016**

(54) PROPHYLACTIC TUBERCULOSIS VACCINE

(75) Inventors: Pere Joan Cardona Iglesias, Badalona (ES); Isabel Amat Riera, Badalona (ES)

(73) Assignee: ARCHIVEL FARMA, S.L., Badalona (ES)

( * ) Notice: Subject to any disclaimer, the term of this patent is extended or adjusted under 35 U.S.C. 154(b) by 472 days.

This patent is subject to a terminal disclaimer.

(21) Appl. No.: 12/447,584

(22) PCT Filed: Oct. 17, 2007

(86) PCT No.: PCT/ES2007/000583

§ 371 (c)(1), (2), (4) Date: Nov. 16, 2009

(87) PCT Pub. No.: WO2008/053055

PCT Pub. Date: May 8, 2008

(65) Prior Publication Data

US 2010/0068258 A1 Mar. 18, 2010

(30) Foreign Application Priority Data

Oct. 30, 2006 (ES) .................................. 200602754

(51) Int. Cl.

*A61K 39/04* (2006.01)
*A61K 39/00* (2006.01)
*A61K 39/02* (2006.01)

(52) U.S. Cl.

CPC ....... *A61K 39/04* (2013.01); *A61K 2039/55555* (2013.01)

(58) Field of Classification Search

CPC ............................... A61K 49/00; A61K 39/04
USPC .............................. 424/9.1, 9.2, 234.1, 248.1
See application file for complete search history.

(56) References Cited

U.S. PATENT DOCUMENTS

| | | | | |
|---|---|---|---|---|
| 6,001,361 | A | 12/1999 | Tan et al. | |
| 8,795,719 | B2 * | 8/2014 | Cardona Iglesias et al. | 424/450 |
| 2002/0094336 | A1 | 7/2002 | Andersen et al. | |
| 2002/0127700 | A1 | 9/2002 | Zhang | |
| 2007/0269501 | A1 | 11/2007 | Cardona Iglesias et al. | |

FOREIGN PATENT DOCUMENTS

| | | | | |
|---|---|---|---|---|
| ES | 2231037 A1 | | 5/2005 | |
| RU | 2153354 C1 | | 7/2000 | |
| WO | WO 00/21983 A1 | | 4/2000 | |
| WO | WO 03/004520 A2 | | 1/2003 | |
| WO | WO 03/018053 A1 | | 3/2003 | |
| WO | WO 03/063897 A1 | | 8/2003 | |
| WO | WO2005/042013 | * | 5/2005 | A61K 39/04 |

OTHER PUBLICATIONS

McMurray, D.N. International Journal for Parasitology, vol. 33, pp. 547-554, 2003.*

Sorensen et al., "Purification and Characterization of a Low-Molecular-Mass T-Cell Antigen Secreted by *Mycobacterium tuberculosis*", Infection and Immunity, vol. 63, No. 5, May 1995, p. 1710-1717.

Kabanov, V.A., "From synthetic polyelectrolytes to polymer-subunit vaccines", Vysokomolekularnye soedinenia, Seria A I seria B, ISSN 1023-3091, vol. 46, No. 5, Abstract.

Sinha et al., "Proteome analysis of the plasma membrane of Mycobacterium tuberculosis", Comparative and Functional Genomics 2002, vol. 3, pp. 470-483.

"Preclinical Testing of New Vaccines for Tuberculosis: A Comprehensive Review", Ian M. Orme, Science Direct, Vaccine 24 (2006) 2-19, Jul. 18, 2005, pp. 1-19.

"Immunology, Resistance to Tuberculosis in Mice Immunized With BCG Disrupted in Oil", Nature Publishing Group, Jun. 22, 1963, vol. 198, pp. 1214-1215.

"Protective Efficacy of Different Cell-Wall Fractions of Mycobacterium Tuberculosis", J.B. Chugii[B] et. al., Folia Microbiol, 37(6), 407-412, 1992.

"Role of Cellwall Vaccine in Prophylaxis of Tuberculosis", D.P. Pal and Shriniwas, Indian J. Med. Res 65, Mar. 3, 1977, pp. 340-345.

"Specific Acquired Resistance in Mice Immunized with Killed Mycobacteria", E.M. Agger et al., Scand., J. Immunol 56, 443-447, 2002.

"Envisioning Future Strategies for Vaccination Against Tuberculosis", Stefan H.E. Kaufmann, 2006 Nature Publishing Group, Aug. 18, 2006.

International Search Report dated Feb. 26, 2008, application No. PCT/ES 2007/000583.

Brosch et al., "A new evolutionary scenario for the *Mycobacterium tuberculosis* complex," PNAS, Mar. 19, 2002, vol. 99, No. 6, pp. 3684-3689.

Gutierrez et al., "Ancient Origin and Gene Mosaicism of the Progenitor of *Mycobacterium tuberculosis*," PLos Pathogens, Sep. 2005, vol. 1, Issue 1, pp. 0055-0061.

McMurray, "Recent progress in the development and testing of vaccines against human tuberculosis," Intl. Journal for Parasitology 33 (2003) 547-554.

Kaufmann, "Report: Clinical Aspects: New issues in tuberculosis," Annals of the Rheumatic Diseases 2004; 63:ii50-ii56.

(Continued)

*Primary Examiner* — Rodney P Swartz
(74) *Attorney, Agent, or Firm* — RatnerPrestia

(57) ABSTRACT

The invention relates to the use of an immunotherapeutic agent containing cell wall fragments of a virulent strain of *Mycobacterium tuberculosis*-complex (MTB-C) for the preparation of a drug for the prophylactic treatment of tuberculosis, in which said agent can be obtained using a method comprising the following steps: cultivate the virulent MTB-C strain over a period equal to or greater than three weeks; and, subsequently, homogenate the cell culture in the presence of a nonionic surfactant.

13 Claims, No Drawings

(56) References Cited

OTHER PUBLICATIONS

Sharp, "*Mycobacterium microti* (Vole Bacillus): a Method for Viable Counts Within 21 Days of Culture," Applied Microbiology, Jun. 1973, vol. 25, No. 6, pp. 1023-1024.
"BCG and Vole-Bacillus Vaccines in the Prevention of Tuberculosis in Adolescents," S. A. Medical Journal, Apr. 21, 1956, pp. 388-391.
Hart et al., "BCG and vole bacillus vaccines in the prevention of tuberculosis in adolescence and early adult life," British Medical Journal, Feb. 1977, 293-295.
Manabe et al., "Naturally Attenuated, Orally Administered *Mycobacterium microti* as a Tuberculosis Vaccine is Better than Subcutaneous *Mycobacterium bovis* BCG," Infection and Immunity, Mar. 2002, vol. 70, No. 3, pp. 1566-1570.

* cited by examiner

PROPHYLACTIC TUBERCULOSIS VACCINE

This application is a U.S. National Phase Application of PCT International Application No. PCT/ES2007/000583, filed Oct. 17, 2007, which claims priority to Spanish Patent Application No. P20062754, filed Oct. 30, 2006, the contents of such applications being incorporated by reference herein in their entirety.

FIELD OF THE ART

The present invention relates to the use of an immunotherapeutic agent based on cell wall fragments of a virulent strain of *Mycobacterium tuberculosis*-complex for the preparation of a drug for the prophylactic treatment of tuberculosis.

PRIOR STATE OF THE ART

Tuberculosis is a chronic infectious disease caused by the *Mycobacterium tuberculosis*-complex (MTB-C) bacilli, which currently include the species *M. tuberculosis, M. bovis, M. microti* and *M. africanum.*

According to the World Health Organization, 8,000,000 new cases of people manifesting the disease are recorded worldwide every year and about 3,000,000 people die. It is considered that there are more than 2,000,000,000 infected people worldwide and that 90-100 million more new infections are generated each year.

The current vaccine which is used in the preventive treatment against tuberculosis is based on bacteria of the strain called BCG (*Bacillus* Calmette-Guerin), an attenuated variant of *M. bovis.*

Various vaccines against tuberculosis based on cell wall fragments of virulent or avirulent strains of *Mycobacterium* are described in the state of the art. It is also described that the adjuvant used in the composition of the vaccine greatly influences the effectiveness thereof.

E. Ribi et al., Nature 1963, 198, pages 1214 to 1215, describe the immunization assays performed with a composition comprising cell wall fragments of the avirulent BCG strain and mineral oil. Said fragments are obtained by homogenization of a culture of the mentioned strain in mineral oil. The composition is more effective than the conventional vaccine (BCG). Nevertheless, it is described in the same article that the cell wall fragments do not induce any immunological response when they are obtained by homogenization in water and in the absence of the mineral oil.

D. P. Pal et al., Indian J. Med. Res. 1977, 65, pages 340 to 345, describe a vaccine prepared with cell wall fragments of the virulent $H_{37}Rv$ strain and mineral oil. In this case the cell wall fragments are obtained by means of homogenization of the dead cells in aqueous phase, and the mineral oil is subsequently added to the composition. It is also described that the cell wall fragments homogenized in aqueous phase are not immunogenic and that the presence of mineral oil is necessary for the vaccine to be effective.

G. K. Khuller et al., Folia Microbiol., 1992, 37, pages 407 to 412, describe the protective efficacy of different fractions of the cell wall of the avirulent $H_{37}Ra$ strain of *M. tuberculosis* formulated with Freund's incomplete adjuvant, which also includes mineral oil.

E. M. Agger et al., Scand. J. Immunol., 2002, 56, pages 443 to 447, describe vaccines comprising cell wall fragments of the virulent $H_{37}Rv$ strain, which are effective when they include the cationic surfactant dimethyldioctadecylammonium bromide as an adjuvant. It is also described that the assays conducted with homogenized *M. tuberculosis* bacilli which do not contain the mentioned adjuvant do not generate levels of resistance against tuberculosis in the murine model.

I. M. Orme Vaccine, 2006, 24, pages 2 to 19, which is a recent review article of new vaccines against tuberculosis, describes that the conventional BCG vaccine is essentially ineffective in protecting adult people against tuberculosis. It is indicated in the same article that several candidates for different types of vaccines (subunit vaccines with proteins, vaccines with DNA, vaccines combined with virus, vaccines with recombinant strains) are being assayed and that new developments are expected.

It is therefore necessary to have a prophylactic vaccine to prevent infections caused by *M. tuberculosis* that is more effective than the current vaccine based on the attenuated BCG strain.

BRIEF DESCRIPTION

The present invention is the use of an immunotherapeutic agent comprising cell wall fragments of a virulent strain of MTB-C for the preparation of a drug for the prophylactic treatment of infections caused by *M. tuberculosis.*

DETAILED DESCRIPTION OF THE INVENTION

Patent application ES2231037-A1 discloses a method for the preparation of an immunotherapeutic agent comprising cell wall fragments of a virulent strain of *Mycobacterium tuberculosis*-complex (MTB-C). It also discloses compositions containing it and the therapeutic application thereof for the combined treatment of tuberculosis in association with other drugs.

The authors of the present invention have discovered the use of said immunotherapeutic agent for the preparation of a drug for the prophylactic treatment of tuberculosis.

The object of the present invention therefore is the use of an immunotherapeutic agent comprising cell wall fragments of a virulent strain of *Mycobacterium tuberculosis*-complex (MTB-C) for the preparation of a drug for the prophylactic treatment of tuberculosis, wherein said agent is obtainable by a method comprising the following steps:

- cultivate the virulent MTB-C strain over a period equal to or greater than three weeks and, subsequently,
- homogenate the cell culture in the presence of a nonionic surfactant.

The virulent strain can be any virulent strain of MTB-C. One of the strains most used by researchers in this field is called $H_{37}Rv$ which, for example, can be freely acquired in the National Collection of Type Cultures (NCTC), London, Great Britain (deposit number NC007416).

The virulent strain can be cultivated by inoculation in culture media well-known by the person skilled in the art, for example Middlebrook 7H10 or 7H11 agar, Sauton's medium or Proskauer-Beck medium.

The culture of the virulent strain is performed over a period equal to or greater than three weeks, preferably comprised between 3 and 4 weeks. The temperature of the culture is preferably maintained between 34° C. and 38° C.

Once the culture ends, the cells are isolated using techniques such as those described, for example, in patent application ES2231037-A1.

The homogenization of the live cells is carried out in the presence of a nonionic surfactant, and preferably in a buffered medium at neutral pH, for example at pH comprised between 6 and 8, such as that provided by PBS buffer (phosphate buffered saline).

The homogenization can be carried out by means of ultrasound sonication, or by means of the use of small beads of approximately 1 mm in diameter, for example, silica or zirconia/silica beads, together with a mechanical homogenizer. A mechanical homogenizer that can be used, for example, is the BioSpec BeadBeater® model.

The MTB-C cells are broken by means of this homogenization process and small cell wall fragments are obtained.

The type of nonionic surfactant used in the homogenization process is preferably selected from the group consisting of alkylphenol ethoxylates, sorbitan ester ethoxylates, and mixtures thereof.

More preferably, the nonionic surfactant is selected from the group of octylphenol ethoxylates. More preferably, octylphenol ethoxylates with an ethylene oxide content comprised between 7 and 8 moles are used, which surfactants can be found on the market under the name Triton X-114®.

The nonionic surfactant content in the homogenization step is preferably comprised between 1% and 10% by weight with respect to the total weight of the homogenate, more preferably between 3% and 6% by weight.

The homogenized mass containing the cell wall fragments is subjected to a conventional treatment to separate and reject the non-fragmented cells and the solubilized components.

Centrifugation at different speeds and washing with buffer solution as described in patent application ES2231027-A1 can be used for example. Sediment containing the cell wall fragments is obtained after performing the mentioned purification processes. Said sediment is dispersed in PBS buffer and is subjected to a conventional treatment to ensure the complete inactivation of the MTB-C cells which may have remained viable after the fragmentation and purification process. The mentioned treatment can be a chemical process, for example by means of treatment with formaldehyde, or a physical process, for example by means of autoclaving or pasteurisation treatment.

The dispersion of cell wall fragments in PBS buffer obtained after the inactivation treatment can be lyophilized to facilitate the storage thereof. To that end, the dispersion can be distributed into vials and lyophilized at a temperature comprised between −15° C. and −25° C. and with a vacuum comprised between 0.1 and 0.5 mbar.

The vials obtained after the lyophilization process contain the immunotherapeutic agent comprising the cell wall fragments of MTB-C, and they are generally stored at very low temperatures, for example at −70° C.

As previously indicated, the object of the invention is the use of the immunotherapeutic agent comprising cell wall fragments of a virulent strain of MTB-C for the preparation of a drug for the prophylactic treatment of tuberculosis, i.e., for the preparation of a prophylactic vaccine against tuberculosis.

The drug for the prophylactic treatment of tuberculosis comprises the immunotherapeutic agent based on cell wall fragments and, optionally, pharmaceutically acceptable diluents, adjuvants and/or excipients. The drug can be in the form of phosphate buffered saline, aqueous solution, emulsion, or in the form of liposomes.

The drug is preferably in the form of liposomes.

The liposomes can be formed using conventional auxiliary lipids and techniques well-known by the person skilled in the art, such as those described in patent application ES2231037-A1.

The liposomes generally include phospholipids, with a neutral and/or negative net charge, and sterols.

The phospholipids used can be, for example: phosphatidylcholine, phosphatidylserine and phosphatidylinositol.

The main component of the liposomes is usually phosphatidylcholine, which can be synthesized or isolated from natural sources. A frequently used commercial product is soy-derived lecithin, which is a complex mixture of phospholipids including thereamong phosphatidylcholine.

The sterols which are used in the preparation of liposomes can be, among others, cholesterol and bile salts.

The liposomes are preferably formed using a mixture of soy-derived lecithin and sodium cholate.

The liposomes can optionally contain additives improving their stability, for example: vitamin E, which acts as a lipid antioxidant.

The liposomes obtained usually have a size distribution in which 99.9% are smaller than 1 micron.

The liposomes can be subjected to lyophilization to thus obtain the immunotherapeutic agent in the form of lyophilized liposomes.

The drug can be administered in the form of a single dose or of several doses, by means of the repetition at certain time intervals. Preferably two doses are administered separated by a period comprised between 2 and 5 weeks, preferably between 3 and 4 weeks.

The drug can be administered in a mucosa, for example, ocular, intranasal, oral, gastric, intestinal, vaginal, or urinary tract mucosa, or parenterally, for example, subcutaneously, intradermally, intramuscularly, intravenously, or intraperitoneally. Parenteral administration is preferred.

The suitable dose depends on several parameters, including thereamong between the method of administration and the subject to be treated, but preferably the dose is comprised between 1 μg and 1000 μg, more preferably between 25 and 700, and even more preferably between 50 μg and 200 μg.

The drug comprising cell wall fragments of a virulent strain of MTB-C can be administered in combination with other prophylactic vaccines against tuberculosis, such as those mentioned in S. H. E. Kaufmann, Nature Rev. Immunol. 2006, 6, 699-704, such as for example the BCG vaccine, subunit vaccines or recombinant BCG vaccines.

The combination of vaccines can be simultaneous or it can be done in two inoculations separated over time. The period between the inoculations can even be several years long.

In the case of inoculations separated over time, first a prophylactic vaccine against tuberculosis is preferably administered, and the drug comprising the cell wall fragments of a virulent strain of MTB-C, which acts as a re-stimulating (boost) agent of the initially inoculated vaccine, is subsequently administered.

It has surprisingly been found that the administration of the drug comprising the immunotherapeutic agent based on cell wall fragments of a virulent strain of MTB-C is able to induce a Th1 type interferon-γ generating response against *M. tuberculosis*-specific antigens. Said antigens include Ag85B and Ag85A, which are part of the complex Ag85, consisting of a family of low molecular weight proteins playing a decisive role in the biosynthesis of the cell wall and produced in considerable amounts when the bacterial cultivation is in the log phase.

It has been observed that the conventional BCG vaccine does not generate an immunoprotective response against antigens of complex Ag85, which could represent a lower protection capability.

It has also been found that the number of viable bacilli present in the lungs of mice vaccinated with said immunotherapeutic agent subsequently infected with the virulent $H_{37}Rv$ strain is less than the number of viable bacilli present in the control mice group, and said number is comparable to that of the mice vaccinated with the conventional BCG vaccine.

The examples below are shown to provide the person skilled in the art with a detailed explanation of specific embodiments within the invention.

EXAMPLE 1

Effectiveness of the Immunotherapeutic Agent as a Prophylactic Vaccine Against the Infection Caused by *M. tuberculosis*

The immunotherapeutic agent used in this example was prepared according to the method described in Example 2 of patent application ES2231037-A1.

The effectiveness of the immunotherapeutic agent based on cell wall fragments of a virulent strain of MTB-C was assayed in C57BL/6 type female mice from 6 to 8 weeks of age and free of specific pathogens.

The mice were divided into three groups of 12 animals each and were subjected to the following vaccination protocol:

1) Without vaccination (control group),
2) Subcutaneously inoculated with two doses of 285 μg of the immunotherapeutic agent obtained in Example 2 of patent application ES2231037-A1 at weeks 3 and 6 of the experiment.
3) Subcutaneously inoculated with a dose of $2\times10^6$ colony forming units of the BCG Danish strain (Statens Serum Institute, Denmark) at week 0 of the experiment.

The virulent strain of *Mycobacterium tuberculosis* ($H_{37}Rv$ Pasteur), which was cultivated in Proskauer-Beck medium until a mid-log phase, was used for the infection and it was stored in aliquots of 1 ml at a temperature of −70° C. until its use.

The mice were aerosol-infected with said virulent strain at week nine of the experiment by means of placing them in a Middlebrook aerosol infection apparatus which provided an inoculum of approximately 10-50 viable bacilli in the lungs of the mice.

The number of viable bacilli in the lungs was determined 3 weeks after the aerosol infection of the animals (week 12 of the experiment) incubating serial dilutions of lung homogenate in Middlebrook 7H11 agar for 4 weeks at 37° C. The lung was homogenized in the presence of 1 ml of twice-distilled water.

The results of Table I express the logarithm of the colony forming units (CFU) per ml which have been identified in the lung:

TABLE I

| Group of mice | Vaccine | $Log_{10}$CFU/ml |
|---|---|---|
| 1 | None (Control Group) | 6.42 ± 0.24 |
| 2 | Liposome-encapsulated immunotherapeutic agent | 5.72 ± 0.30 |
| 3 | BCG | 5.71 ± 0.58 |

The differences between the result of the group of mice which have not been vaccinated and the results of the groups vaccinated are statistically significant.

It can be observed that in the lung of the group of mice vaccinated with the liposome-encapsulated immunotherapeutic agent a smaller number of viable bacilli is detected than in the lung of the mice not vaccinated, and a substantially identical number to that of the mice vaccinated with the conventional BCG vaccine.

Therefore, the vaccination with the immunotherapeutic agent based on cell wall fragments of a virulent strain of MTB-C achieves protecting against infections caused by *M. tuberculosis*.

EXAMPLE 2

Effectiveness of the Immunotherapeutic Agent as a Generator of a Th1 Response Specific Against Infection Caused by *M. tuberculosis*

The immunotherapeutic agent used in this example was prepared according to the method described in Example 2 of patent application ES2231037-A1.

The effectiveness of the immunotherapeutic agent based on cell wall fragments of a virulent strain of MTB-C was assayed in C57BL/6 type female mice from 6 to 8 weeks of age and free of specific pathogens in an ex vivo experiment.

The mice were divided into groups of 4 animals each and were subjected to the following inoculation schedule:

1) Subcutaneously inoculated with saline at weeks 3 and 6 of the experiment (control group),
2) Subcutaneously inoculated with two doses of 285 μg of the immunotherapeutic agent obtained in Example 2 of patent application ES2231037-A1 at weeks 3 and 6 of the experiment.
3) Subcutaneously inoculated with a dose of $2\times10^6$ colony forming units of the BCG Danish strain (Statens Serum Institute, Denmark) at week 0 of the experiment, and with saline at weeks 3 and 6 of the experiment.
4) Subcutaneously inoculated with $2\times10^6$ colony forming units of the virulent strain of *Mycobacterium tuberculosis* ($H_{37}Rv$ Pasteur) at week 3 of the experiment, and with saline at week 6 of the experiment.

The mice were sacrificed at week 7, and their spleens were extracted and immersed in tubes containing 5 ml of L-glutamine-RPMI (Gibco). The tubes were kept in ice until the end of the experiment. The spleens were mechanically disintegrated and the suspension was filtered through a nylon mesh 70 μm in diameter. Then it was centrifuged for 10 minutes at 300 g. The pellets were reconstituted with 15 ml of a solution consisting of Tris and ammonium chloride in twice-distilled water to perform lysis on the cells. After 8 minutes they were washed with 20 ml of L-glutamine-RPMI and centrifuged for 10 minutes at 300 g.

The obtained pellets were resuspended with 5 ml of L-glutamine-RPMI, and the suspension was filtered through a nylon mesh 70 μm in diameter. The cells were counted with the Neubauer chamber.

The cells from the spleen of the mice were seeded on dishes at a ratio of $1\times10^5$ cells/well and were cultivated with 200 μl of the complete culture medium (CCM) consisting of L-glutamine-RPMI supplemented with inactivated foetal calf serum, penicillin, streptomycin, sodium pyruvate, and 2-mercaptoethanol, or with 200 μl of complete culture medium (CCM) supplemented with *M. tuberculosis* antigens: 10 μg/ml of the antigen PPD (Statens Serum Institut, Denmark) and 5 μg/ml of ESAT-6, Ag85A and Ag85B (Lionex Diagnostics and Therapeutics GmbH, Federal Republic of Germany).

The cells were incubated at 37° C. in an atmosphere with 5% $CO_2$. After 96 hours, the dishes were centrifuged for 10 minutes at 300 g, and the supernatant of each of them was collected.

The supernatants were frozen and after remaining in said state at least 24 hours, the interferon-γ content was analyzed applying the double sandwich ELISA technique and using a monoclonal antibody specific for murine interferon-γ (Diaclone).

Table II shows the average interferon-γ concentration expressed as $\log_{10}$ pg/ml which was induced in each of the groups of mice against the *M. tuberculosis* antigens:

TABLE II

| Group | Inoculum | Antigens | | | | |
|---|---|---|---|---|---|---|
| | | Control | PPD | ESAT-6 | Ag85B | Ag85A |
| 1 | Control | 0 | 0 | 0 | 0 | 0 |
| 2 | Liposome-encapsulated immunotherapeutic agent | 0 | 2.57 | 0 | 2.69(1) | 2.53(1) |
| 3 | BCG | 0 | 2.01(3) | 0 | 0 | 0 |
| 4 | $H_{37}Rv$ | 0 | 3.06(3) | 2.86(2)(3) | 2.76(3) | 2.50(3) |

(1)Statistically significant differences between Group 2 and Group 3
(2)Statistically significant differences between Group 2 and Group 4
(3)Statistically significant differences between Group 3 and Group 4

The results of Table II show that the two inoculations performed with the liposome-encapsulated immunotherapeutic agent based on cell wall fragments of a virulent strain of *M. tuberculosis* are able to induce the production of interferon-γ against *M. tuberculosis*-specific antigens. This means that they induce a Th1 type protective response.

Particularly, the response induced by the group of mice inoculated with the liposome-encapsulated immunotherapeutic agent against the antigens PPD, Ag85B and Ag85A presents no significant differences with the response of the group of mice inoculated with the virulent $H_{37}Rv$ strain of *M. tuberculosis*. Said response is better than the response of the group of mice inoculated with the BCG strain, which is the conventional vaccine, since it only induces a response against PPD and not against Ag85B and Ag85A.

Only the group of mice inoculated with the virulent strain was able to induce a response against the antigen ESAT-6.

Therefore, the immunotherapeutic agent based on cell wall fragments of a virulent strain of *M. tuberculosis* is able to induce a Th1 type protective response against *M. tuberculosis*-specific antigens, which is an indicator that it can be used effectively to prevent infections caused by *M. tuberculosis*.

The invention claimed is:

1. A method for the prophylactic treatment of tuberculosis, which comprises the administration of an immunotherapeutic agent comprising cell wall fragments of a virulent strain of *Mycobacterium tuberculosis*, wherein said agent is obtainable by a method comprising the following steps:

(i) cultivating the virulent strain of *Mycobacterium tuberculosis* over a period equal to or greater than three weeks and, subsequently, (ii) homogenizing the cell culture in the presence of a nonionic surfactant selected from the group consisting of alkylphenol ethoxylates, sorbitan ester ethoxylates, and mixtures thereof to obtain a homogenized mass comprised of cell wall fragments, non-fragmented cells and solubilized components, (iii) centrifuging the homogenized mass obtained in step (ii) to separate the cell wall fragments from the non-fragmented cells and the solubilized components, wherein the homogenized mass is centrifuged at a speed slower than 5,000 rpm to obtain a supernatant and a first sediment which contains the non-fragmented cells and which is rejected, and wherein the resulting supernatant is recentrifuged at a speed higher than 15,000 rpm to separate the solubilized elements that concentrate in the supernatant liquid, which is rejected, and the cell wall fragments, which concentrate in a second sediment obtained from the recentrifugation, (iv) subjecting the cell wall fragments separated in step (iii) to chemical or physical treatment to inactivate the eventual virulent strain cells that they eventually contain, and (v) drying the obtained immunotherapeutic agent by means of lyophilization.

2. The method according to claim 1, wherein the culture period is comprised between 3 and 4 weeks.

3. The method according to claim 1, wherein the nonionic surfactant is selected from the group of octylphenol ethoxylates.

4. The method according to claim 1, wherein the nonionic surfactant is Selected from the octylphenol ethoxylates with an ethylene oxide content comprised between 7 and 8 moles.

5. The method according to claim 1, wherein the homogenization is performed in a buffered medium at neutral pH.

6. The method according to claim 1, wherein the immunotherapeutic agent is in the form of liposomes.

7. The method according to claim 1, wherein the immunotherapeutic agent is administered in the form of a single dose or of several doses.

8. The method according to claim 7, wherein the immunotherapeutic agent is administered in two doses.

9. The method according to claim 8, wherein the doses are administered separated by a period comprised between 2 and 5 weeks.

10. The method according to claim 1, wherein the immunotherapeutic agent is administered in combination with other prophylactic vaccines against tuberculosis.

11. The method according to claim 10, wherein the vaccines are combined in two inoculations separated over time.

12. The method according to claim 11, wherein first a prophylactic vaccine against tuberculosis is administered, and the immunotherapeutic agent comprising the cell wall fragments of the virulent strain of *Mycobacterium tuberculosis* is subsequently administered.

13. The method according to claim 1, wherein the virulent strain of *Mycobacterium tuberculosis* is $H_{37}Rv$ Pasteur.

* * * * *